US009082167B2

(12) United States Patent
Bruder et al.

(10) Patent No.: US 9,082,167 B2
(45) Date of Patent: Jul. 14, 2015

(54) METHOD FOR ITERATIVE IMAGE RECONSTRUCTION FOR BI-MODAL CT DATA

(71) Applicant: SIEMENS AKTIENGESELLSCHAFT, Munich (DE)

(72) Inventors: Herbert Bruder, Hoechstadt (DE); Ernst Klotz, Uttenreuth (DE); Martin Petersilka, Adelsdorf (DE); Rainer Raupach, Heroldsbach (DE); Harald Schöndube, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 254 days.

(21) Appl. No.: 13/776,937

(22) Filed: Feb. 26, 2013

(65) Prior Publication Data
US 2013/0259342 A1 Oct. 3, 2013

(30) Foreign Application Priority Data

Mar. 28, 2012 (DE) .......................... 10 2012 204 977

(51) Int. Cl.
*G06K 9/00* (2006.01)
*G06T 7/00* (2006.01)
*G06T 11/00* (2006.01)
*A61B 6/00* (2006.01)

(52) U.S. Cl.
CPC ............... *G06T 7/0012* (2013.01); *A61B 6/507* (2013.01); *G06T 11/003* (2013.01); *G06T 11/006* (2013.01); *G06T 2211/424* (2013.01)

(58) Field of Classification Search
None
See application file for complete search history.

(56) References Cited

U.S. PATENT DOCUMENTS

| 8,306,303 | B2 | 11/2012 | Bruder et al. |
| 2007/0268997 | A1* | 11/2007 | Zhu et al. ........................ 378/7 |
| 2010/0166277 | A1 | 7/2010 | Raupach |
| 2010/0177973 | A1* | 7/2010 | Wedi et al. .................... 382/233 |
| 2010/0246917 | A1* | 9/2010 | Bruder et al. ................. 382/131 |

(Continued)

FOREIGN PATENT DOCUMENTS

DE 102007061935 A1 6/2009
DE 102008063311 A1 7/2010

(Continued)

OTHER PUBLICATIONS

"Adaptive iterative Reconstruction", H. Bruder et al.; H. Bruder et al., "Adaptive iterative Reconstruction", Proceedings SPIE MedicalImaging, 2011; 2011.
German Priority Application No. 102012204977.0 filed Mar. 28, 2012.

*Primary Examiner* — Shervin Nakhjavan
(74) *Attorney, Agent, or Firm* — Harness, Dickey & Pierce

(57) ABSTRACT

A method is disclosed for the reconstruction of image data of an examination object from measurement data. First and second image data are reconstructed from the measurement data with a first and second respective image characteristic, with an enhanced signal-to-noise ratio of the second image characteristic relative to the first image characteristic. Enhanced image data is calculated using an iterative algorithm using the first and the second image data. In the case of the iterative algorithm, a low pass is applied to a difference between the first image data and the image data of an iteration cycle, and a high pass to a difference between the second image data and the image data of the iteration cycle.

26 Claims, 3 Drawing Sheets

(56) References Cited

U.S. PATENT DOCUMENTS

2011/0052030 A1* 3/2011 Bruder et al. .............. 382/131
2011/0293159 A1 12/2011 Bruder et al.
2012/0121148 A1 5/2012 Bruder et al.
2014/0107467 A1* 4/2014 Felmlee et al. .............. 600/411

FOREIGN PATENT DOCUMENTS

| | | |
|---|---|---|
| DE | 102010022306 A1 | 12/2011 |
| DE | 102010043975 A1 | 5/2012 |
| DE | 102011006188 A1 | 10/2012 |

* cited by examiner

METHOD FOR ITERATIVE IMAGE RECONSTRUCTION FOR BI-MODAL CT DATA

PRIORITY STATEMENT

The present application hereby claims priority under 35 U.S.C. §119 to German patent application number DE 10 2012 204 977.0 filed Mar. 28, 2012, the entire contents of which are hereby incorporated herein by reference.

FIELD

At least one embodiment of the invention generally relates to a method for the reconstruction of image data of an examination object from measurement data, wherein the measurement data was collected previously during a relative rotational movement between a radiation source of a computed tomography system and the examination object.

BACKGROUND

Tomographic imaging methods are characterized by the possibility of examining internal structures of an examination object without having to perform invasive interventions thereupon. A possible type of tomographic image generation consists of recording a number of projections of the object to be investigated from various angles. A two-dimensional view or a three-dimensional volume image of the examination object can be calculated from these projections.

Computed tomography is an example of such a tomographic imaging method. Various methods for scanning an examination object with a CT system are known. For example, circular scans, sequential circular scans with a feed or spiral scans are used. Other kinds of scans which are not based on circular movements are also possible, for example scans with linear segments. Absorption data of the examination object is recorded from various angles with the aid of at least one X-ray source and at least one detector on the opposite side and this absorption data or these projections collected in this way are merged to form sectional views through the examination object by way of corresponding reconstruction methods.

To reconstruct computed tomographic images from X-ray CT data sets of a computed tomography device (CT device), i.e. from the recorded projections, a so-called Filtered Back Projection (FBP) is used as a standard method today. After data acquisition a so-called "rebinning" step is usually performed, in which the data generated with the fan-shaped beam spreading out from the source is rearranged in such a way that it exists in a form as if the detector were being hit by parallel X-rays falling in the direction of the detector. The data is then transformed into the frequency range. Filtering takes place in the frequency range, and then the filtered data is back-transformed. With the aid of the data rearranged and filtered in this way a back projection then takes place onto the individual voxels inside the volume of interest. However, on account of their approximative working method there are problems with the classic FBP methods with so-called low-frequency hollow-cone artifacts and spiral artifacts. Furthermore, with classic FBP methods the image sharpness is linked to the image noise. The greater the sharpness achieved, the greater the image noise and vice versa.

The FBP method is part of the group of approximative reconstruction methods. In addition, there is the group of exact reconstruction methods, but this is scarcely used at the present time. Finally, a third group of reconstruction methods comprises the iterative methods.

With iterative reconstruction methods at least some of the aforementioned limitations of FBP can be remedied. With such an iterative reconstruction method, initial image data is first reconstructed from the projection measurement data. For example, a folding back projection method can be used for this purpose. The iterative reconstruction method subsequently creates gradually enhanced image data. For example, synthetic projection data can be created from the initial image data using a "projector", a projection operator which is intended to map the measurement system as well as possible mathematically. The difference from the measured values is then back-projected using the operator adjointed to the projector and in this way a residual image is reconstructed with which the initial image is updated. The updated image data can in turn be used in a subsequent iteration step to create new synthetic projection data with the aid of the projection operator, therefrom to establish the difference from the measurement signals again and to calculate a new residual image with which the image data of the current iteration level can be improved again, etc. Using such a method, image data can be reconstructed which has relatively good image sharpness and nevertheless low image noise. Examples of iterative reconstruction methods are Algebraic Reconstruction Technology (ART), Simultaneous Algebraic Reconstruction Technology (SART), Iterative Filtered Back Projection (IFBP), as well as statistical iterative image reconstruction technologies.

SUMMARY

At least one embodiment of the invention is to present a method for the iterative reconstruction of CT images. In addition, a corresponding processing unit, a CT system, a computer program and a data medium for a computer program are to be presented.

A processing unit, a CT system, a computer program and a data medium are disclosed. Advantageous embodiments and developments are the subject of subclaims.

In the method according to at least one embodiment of the invention for image reconstruction the measurement data for a relative rotational movement between a radiation source of a computed tomography system and the examination object were previously recorded. First image data with a first image characteristic and second image data with a second image characteristic are reconstructed from the measurement data. The second image characteristic is characterized by an enhanced signal-to-noise ratio compared with the first image characteristic. Using the first and second image data enhanced image data is calculated using an iterative algorithm. For the iterative algorithm the following are used:
  a low pass related to a difference between the first image data and image data of an iteration cycle, and
  a high pass related to a difference between the second image data and the image data of the iteration cycle.

BRIEF DESCRIPTION OF THE DRAWINGS

The invention is explained in more detail below on the basis of an example embodiment. The figures show.

DETAILED DESCRIPTION OF THE EXAMPLE EMBODIMENTS

Figure 1:
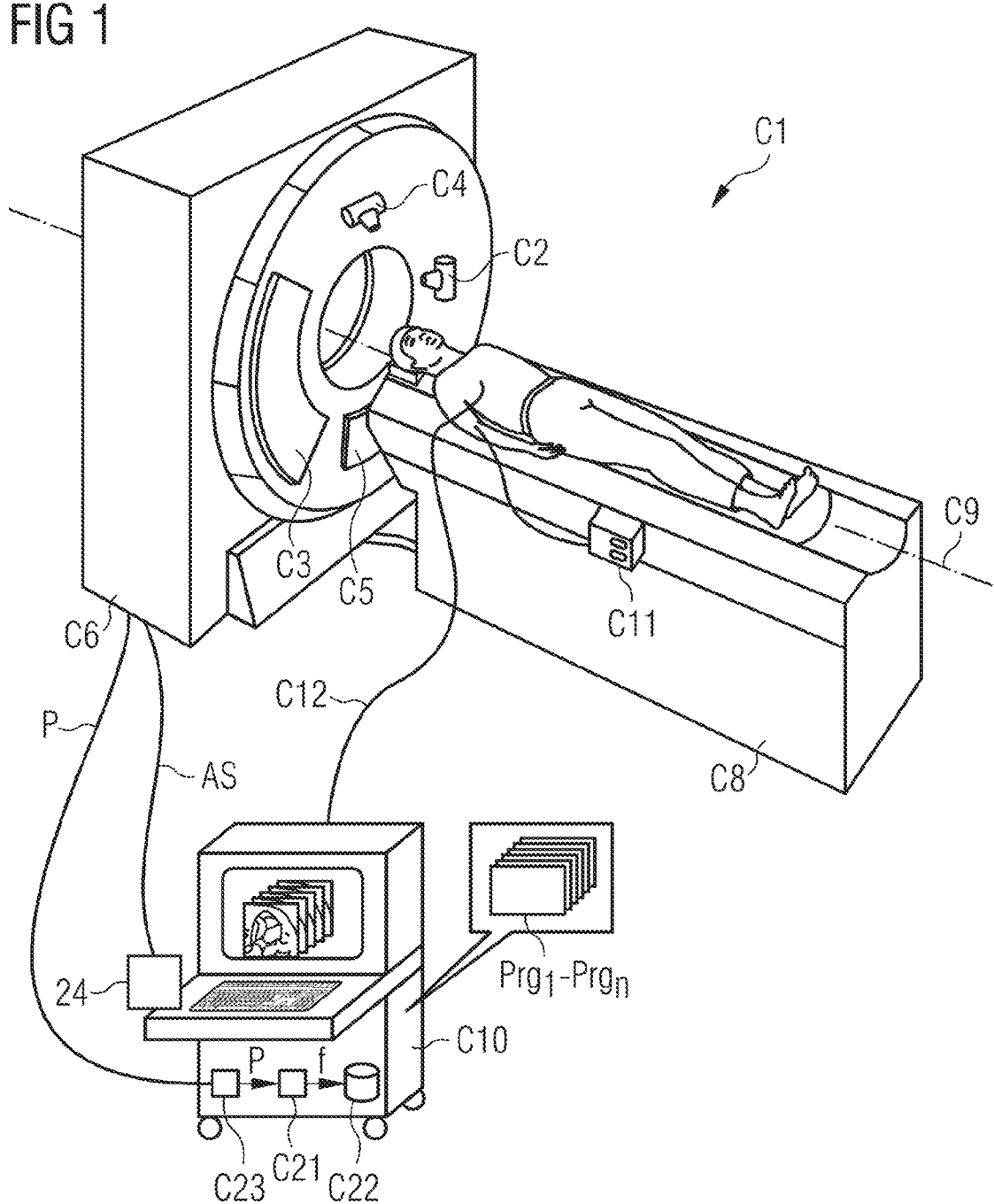
FIG. 1: a first schematic diagram of an example embodiment of a computed tomography system with an image reconstruction component.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the method according to at least one embodiment of the invention for image reconstruction the measurement data for a relative rotational movement between a radiation source of a computed tomography system and the examination object were previously recorded. First image data with a first image characteristic and second image data with a second image characteristic are reconstructed from the measurement data. The second image characteristic is characterized by an enhanced signal-to-noise ratio compared with the first image characteristic. Using the first and second image data enhanced image data is calculated using an iterative algorithm. For the iterative algorithm the following are used:

a low pass related to a difference between the first image data and image data of an iteration cycle, and
 a high pass related to a difference between the second image data and the image data of the iteration cycle.

First of all duplicate image data is therefore available. This relates to the same examination object or to the same view of this examination object. Each element of the examination object or the view of the examination object is therefore reproduced both in the first and in the second image data. With regard to their properties, both sets of image data differ from each other, and they therefore display a different image characteristic. The second image data has a better signal-to-noise ratio than the first image data. This preferably applies to each pixel, i.e. the local signal-to-noise ratio of the second image data is higher than that of the first image data. However, at least there is a better signal-to-noise ratio of the second image data compared with the first image data averaged over all the pixels.

To calculate the first and second image data e.g. the same measurement data and a different reconstruction method can be used. It is also possible that the measurement data which is used for the first image data represents a subset of the measurement data of the second image data. Finally, the measurement data of the first image data and of the second image data may not display any overlapping either. In both the aforementioned examples the reconstruction method of the first and the second image data may be the same or different. In addition, the first and second image data need not be calculated independently of each other; it is therefore possible e.g. to reconstruct the first image data first and then to calculate the second image data using the first image data, without the measurement data being used again for this.

The first and the second image data are now merged to form enhanced image data by way of an iterative algorithm. In this algorithm on the one hand there is a difference between the first image data and the image data of an iteration cycle, and on the other hand between the second image data and the image data of the iteration cycle. In the case of the first image data and the second image data the formation of the difference takes place with regard to the same image data, namely the image data of an iteration cycle. This is image data which was already calculated within the framework of iterative image reconstruction. A low pass is applied to the first-mentioned difference and a high pass to the second-mentioned difference. By this, certain frequency ranges of the first and second image data can be selectively included in the enhanced image data. It is possible that the first and the second image data are also included in the iterative algorithm otherwise than by way of the differences explained.

It is particularly advantageous if the enhanced image data has an enhanced signal-to-noise ratio compared with the first image data. This means that advantages of the second image data can be transferred to the final image.

In a development of at least one embodiment of the invention in the case of the iterative algorithm, a non-linear operator is applied to the image data of the iteration cycle, which performs edge-preserving smoothing. Such an operator may be referred to as a regularization operator. Advantageously the non-linear operator comprises filtering dependent on a contrast-to-noise. This enables noise reduction while retaining sharpness at the same time.

In an embodiment of the invention in the case of the iterative algorithm the following are added up:
- the image data of the iteration cycle,
- the result of the application of the low pass to the difference between the first image data and the image data of the iteration cycle,
- the result of the application of the high pass to the difference between the second image data and the image data of the iteration cycle, and
- the result of the application of the non-linear operator.

This addition can be weighted if necessary.

Preferably the first image data has better spatial resolution and/or better time resolution and/or better spectral resolution and/or fewer image artifacts compared with the second image data. The image characteristic of the first image data may therefore be better in one or more of the aforementioned respects than that of the second image data. Which positive properties the first image data has compared with the second image data depends on the actual application.

Advantageously the second image data is used as image data of the zero iteration. The first iteration image data is therefore calculated on the basis of the second image data. The first image data is then only used after the calculation of the first iteration image data.

The method can be applied to dual-energy measurements. Image data is reconstructed for a first and for a second X-ray energy; the image data of the first X-ray energy is used as first image data, and a combination of the image data of the first X-ray energy and the image data of the second X-ray energy as the second image data; enhanced image data of the first X-ray energy is calculated using the iterative algorithm. Preferably the same approach is then taken with regard to the image data of the second energy. Based on the enhanced image data of the first energy and the enhanced image data of the second energy, material segmentation can then take place.

The method can also be applied to a high-resolution measurement with a reduced detector aperture. The measurement data of the high-resolution measurement is used as the first image data, and the measurement data of a standard measurement as the second image data.

The iterative image reconstruction described is also applicable to perfusion measurements. A series of image data corresponding to consecutive time points is reconstructed; an element of the series is used as the first image data, and a combination of several elements of the series as the second image data. This approach is preferably taken with regard to most of the individual elements in the series.

The method is also suitable for moving examination objects. The first image data is reconstructed from a first segment of the measurement data, and the second image data from an enlarged segment of the measurement data compared to the first image data. Preferably the first segment corresponds to a minimum measurement data area required for image reconstruction.

An additional area of application is phase-contrast CT, in which an absorption CT image is used as the first image data and a phase-contrast CT image as the second image data. While in the first case the properties of matter are exploited to absorb X-rays, the phase-contrast CT takes advantage of the property of matter to shift the phase relationship of X-rays. A disadvantage of phase-contrast CT images is that they exhibit increased noise at very low frequencies. At the other frequencies, and therefore in by far the majority of the frequency range, the signal-to-noise ratio is better compared to the absorption CT images.

Another example embodiment of the invention are two-phase or multi-phase measurements. Thus the first measurement data acquisition can take place before a contrast agent is administered and at least one additional measurement data acquisition after a contrast agent has been administered; native image data is reconstructed from the measurement data of the first measurement data acquisition, and one or more additional items of image data from the measurement data of the at least one additional measurement data acquisition; the first image data corresponds to the native image data or to one of the one or more additional items of image data, and the second image data to a combination of the first image data with the one or more additional items of image data. An image of the examination object from before administration of the contrast agent therefore exists, the so-called native image. Furthermore, there are one or more additional images which show the examination object after administration of the contrast agent. If the native image data is used as the first image data, through the application of the iterative algorithm this image can be improved with regard to its signal-to-noise ratio. The same applies to an image which shows the examination object after administration of the contrast agent, if such an image is used for the first image data.

Furthermore, at least one embodiment of the invention is also applicable to situations in which a subtraction between two CT images is to be calculated. Thus, a first measurement data acquisition can take place before the administration of a contrast agent, and a further measurement data acquisition after the administration of the contrast agent; native image data is reconstructed from the measurement data of the first measurement data acquisition, and additional image data from the measurement data of the additional measurement data acquisition; the first image data corresponds to a difference between the native and the additional image data, and the second image data to a combination of the first image data with the additional image data. Alternatively, it is also possible to first improve the native and additional image data individually by way of the iterative algorithm, and then to form the difference.

In the simplest case, the combination is an average determination. Preferably a weighted sum is used. It is particularly advantageous if a location-dependent weighting takes place; i.e. a constant factor is not used as a weighting factor for an image but rather the strength of the weighting may vary from pixel to pixel.

It is particularly advantageous if the low pass is adjusted to the modulation transfer function of the first image data. This adjustment may in particular be such that the function bringing about the low-pass filtering is identical to the modulation transfer function of the first image data or of a convolution kernel used for the reconstruction of the first image data. Preferably the low pass has approximately the same threshold frequency as this modulation transfer function. The threshold frequency is the frequency at which the modulation transfer function reaches the value zero. Below this frequency the use of a rectangular function is favorable for the low pass.

In an embodiment of the invention the high pass is complementary to the low pass. This avoids a shift of CT values when image data is calculated repeatedly by way of the iterative algorithm. If the low pass is adjusted to the modulation transfer function, this also applies to the high pass accordingly.

The processing unit according to at least one embodiment of the invention serves to reconstruct image data of an examination object from measurement data of a CT system. It has devices for performing the method described. In particular it may include a program memory for the storage of program code, wherein—if applicable, among other things—program code of a computer program is present which is suitable for performing a method of the aforementioned kind or for effecting or controlling this performance, if the computer program is executed on a computer. The processing unit can also be realized by way of a plurality of interconnected devices at various locations. This corresponds to a distribution of the functionality of the processing unit across several components. Advantageously the processing unit is additionally in a position to control a measurement procedure of the CT system.

The CT system according to at least one embodiment of the invention comprises such a processing unit. In addition, it may contain other components which e.g. are required to record measurement data.

The computer program according to at least one embodiment of the invention has program code which effects the performance of a method of the kind described when the computer program is executed on a computer.

The data medium according to at least one embodiment of the invention, which can be read by a computer, saves program code of a computer program which effects the performance of a method of the kind described when the computer program is executed on a computer.

In FIG. 1 first of all a first computed tomography system C1 with an image reconstruction device C21 is shown schematically. This is a CT device of the so-called third generation to which the invention is not restricted, however. In the gantry case C6 there is a closed gantry not visible here, on which a first X-ray tube C2 is arranged with a detector C3 on the opposite side. Optionally in the CT system shown here there is a second X-ray tube C4 with a detector C5 arranged on the opposite side, so that a higher time resolution can be achieved by way of the additionally available emitter/detector combination, or when various X-ray energy spectra are used in the emitter/detector systems, "dual energy" examinations can also be performed.

Furthermore, the CT system C1 has an examination table C8 on which a patient can be pushed into the measuring field along a system axis C9, also referred to as the z-axis, during the examination. However, it is also possible that the scan itself takes place solely in the examination area concerned as a purely circular scan without forward feeding of the patient. The movement of the examination table C8 relative to the gantry is effected by suitable mechanization. During this movement the X-ray source C2 or C4 respectively rotates around the patient. Opposite the X-ray source C2 or C4, the detector C3 or C5 operates in parallel in order to acquire projection measurement data which is then used for the reconstruction of views.

As an alternative to a sequential scan in which the patient is gradually pushed through the examination field between the individual scans, of course there is also the possibility of a spiral scan in which the patient is constantly pushed along the system axis C9 through the examination field between X-ray tube C2 or C4 and detector C3 or C5 during the rotating scan with the X-rays. As a result of the movement of the patient along the axis C9 and the simultaneous rotation of the X-ray source C2 or C4, during a spiral scan a helix path is produced for the X-ray source C2 or C4 relative to the patient during measurement. This path may also be obtained by moving the gantry along the axis C9 while the patient remains static. Furthermore, it is possible to move the patient back and forth constantly and if necessary periodically between two points.

The CT system C1 is controlled by a control and processing unit C10 with computer program code Prg1 to Prgn present in a storage device. It is pointed out that this computer program code Prg1 to Prgn can of course also be contained on an external storage medium and if need be can be loaded into the control and processing unit C10.

From the control and processing unit C10 acquisition control signals AS can be transmitted via a control interface 24 in order to control the CT device in accordance with certain measurement protocols. The acquisition control signals AS relate to e.g. the X-ray tubes C2 and C4, wherein requirements for their performance and the times of their switching on and off can be set, as well as the gantry, wherein requirements for its rotation speed can be set, as well as the table forward feed.

As the control and processing unit C10 has an input console, measurement parameters can be entered by a user or operator of the CT device, which then control data acquisition in the form of acquisition control signals AS. Information about measurement parameters currently used can be displayed on the screen of the control and processing unit C10; in addition, further information relevant to the operator can be displayed.

The projection measurement data p or raw data acquired from the detector C3 or C5 is transferred via a raw data interface C23 to the control and processing unit C10. This raw data p is then, if need be after appropriate preprocessing, further processed in an image reconstruction component C21. In this example embodiment the image reconstruction component C21 is realized in the form of software on a processor in the control and processing unit C10, e.g. in the form of one or more of the computer program codes Prg1 to Prgn. With regard to image reconstruction, as already explained with regard to the control of the measurement procedure, the computer program codes Prg1 to Prgn are also contained on an external storage medium and can be loaded into the control and processing unit C10 if necessary. Furthermore, it is possible that the control of the measurement procedure on the one hand and image reconstruction on the other hand are performed by different processing units.

The image data f reconstructed from the image reconstruction component C21 is then stored in a storage device C22 of the control and processing unit C10 and/or displayed on the screen of the control and processing unit C10 in the usual manner. It can also be fed via an interface not shown in FIG. 1 into a network connected to the computed tomography system C1, for example a radiology information system (RIS), and stored in a mass storage device accessible there or displayed as images.

In addition, the control and processing unit C10 can also perform the function of an ECG, wherein a lead C12 is used to derive the ECG potential between patient and control and processing unit C10. In addition, the CT system C1 shown in FIG. 1 also has a contrast agent injector C11, via which in addition contrast agent can be injected into the bloodstream of the patient, so that e.g. the vessels of the patient, in particular the ventricles of the beating heart, can be better displayed. In addition, there is also the possibility of performing perfusion measurements, for which the proposed method is likewise suitable.

The control and processing unit C10—contrary to what is shown in FIG. 1—naturally need not be located in the vicinity of the remaining components of the CT system C1. Instead it is possible to accommodate it in another room or at a more distant location. The transfer of the raw data p and/or the acquisition signals AS and/or the ECG data can take place via leads or alternatively via radio.

Figure 2:
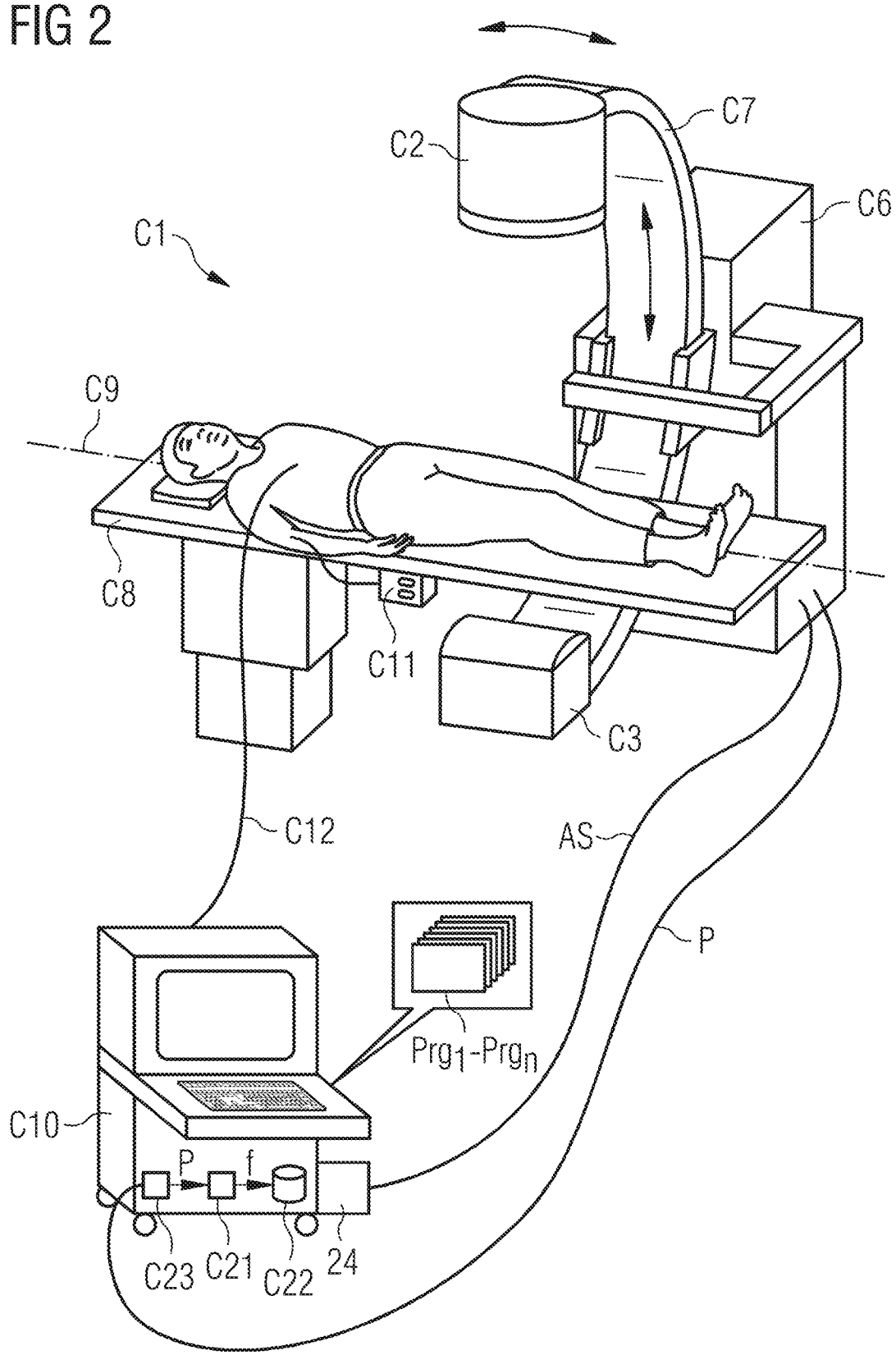
FIG. 2: a second schematic diagram of an example embodiment of a computed tomography system with an image reconstruction component.

FIG. 2 shows a C-arm system, in which in contrast to the CT system in FIG. 1 the case C6 supports the C-arm C7, to which on the one hand the X-ray tube C2 and on the other hand the detector C3 on the opposite side are fastened. The C-arm C7 is likewise swiveled around a system axis C9 for a scan, so that a scan can take place from a variety of angles and corresponding projection data p can be determined from a variety of projection angles. Like the CT system in FIG. 1, the C-arm system C1 in FIG. 2 also has a control and processing unit C10 of the kind described in FIG. 1.

Embodiments of the invention can be used in both of the systems shown in FIGS. 1 and 2. Furthermore, in principle it can also be used for other CT systems, e.g. for CT systems with a detector forming a complete ring.

Figure 3:
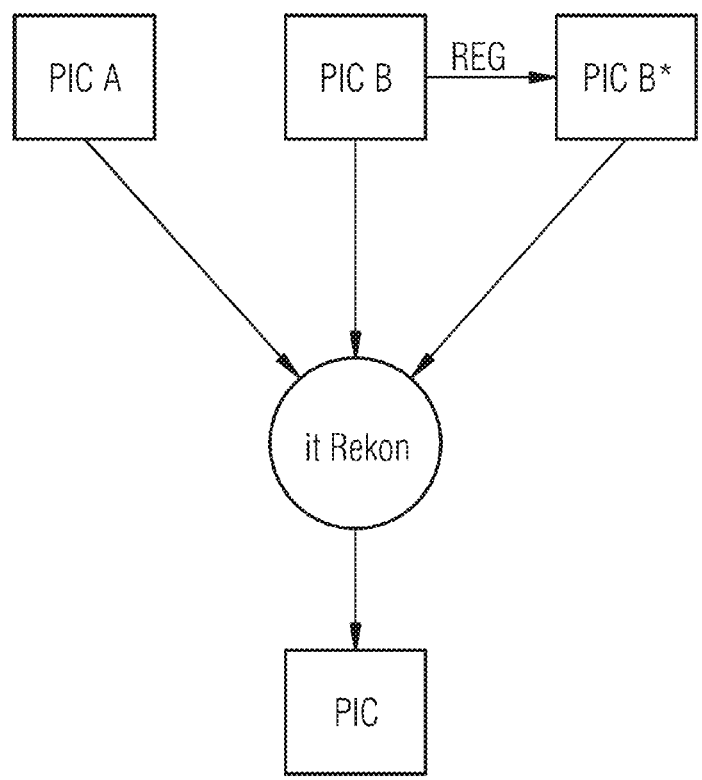
FIG. 3: a flow chart for iterative image reconstruction.

Below it is assumed that a CT measurement has taken place and image data was reconstructed from the measurement data. The sequence of the method is shown in FIG. 3. Not only one image but two images PIC A and PIC B are present which show the same view of the examination object. First and second image data is therefore available for the same view of the examination object. This is of variable quality: PIC A has a poorer signal-to-noise ratio but has other advantageous image properties. Such an advantageous image property may e.g. consist of high spatial resolution, high time resolution, high spectral resolution, or an absence or reduction of image artifacts. In comparison, the image PIC B does not have these advantageous properties or at least has them to a lesser extent, but has a better signal-to-noise ratio.

The images PIC A and PIC B can be calculated in a manner known per se, e.g. by way of an FBP (Filtered Back Projection) method. Two-dimensional sectional views or three-dimensional volume images of the examination object may be involved.

The aim of the approach described below is to obtain a final image PIC, using the images PIC A and PIC B with their different image characteristics, which combines the advantages of both images PIC A and PIC B, i.e. the good signal-to-noise ratio of the image PIC B and the other good image qualities of image PIC A. For this purpose the image PIC B is first modified in a regularization step REG by smoothing noise; the result of this modification is the image PIC B*. The images PIC A, PIC B and PIC B* then form the basis of an iterative reconstruction it Rekon, which is based on the following update formula:

$$f_{k+1} = f_k + \alpha_1 \cdot \Lambda \otimes (PICA - f_k) + \alpha_2 \cdot \Lambda^* \otimes (PICB - f_k) - \gamma \cdot \Lambda R (f_k)$$ Equation (1):

$f_{k+1}$ is the image of the (k+1)-th iteration. The k-th iteration is calculated from the image $f_k$.

The image PIC B is used as image $f_0$ for the first iteration. This can also be seen from FIG. 3: the step REG corresponds to the application of the regularization operator $\gamma \cdot \Lambda R$ (to be explained in more detail) to the image PIC B. In the first iteration the last part corresponds to the equation (1), $\gamma \cdot \Lambda R (f_k)$, hence $\gamma \cdot PICB^*$. In the additional iterations however, PIC B* is no longer used at this point but the respective $f_k$ of the preceding iteration.

In each iteration the update image $f_k$ is combined in linear fashion from three components. The following contribute to this: the correction image $\alpha_1 \cdot \Lambda \otimes (PICA - f_k) + \alpha_2 \cdot \Lambda^* \otimes (PICB - f_k)$, the image $f_k$ from the previous iteration and the regularization image $\gamma \cdot \Lambda R(f_k)$. The parameters $\alpha_1$, $\alpha_2$ and $\gamma$ control the relative weighting of the correction term and the regularization contribution.

The operators $\Lambda$ and $\Lambda^*$ are each band-pass filters in the frequency range; $\otimes$ is the convolution operator. $\Lambda$ is a low pass, $\Lambda^*$ a high pass. Both the operators $\Lambda$ and $\Lambda^*$ complement each other, i.e. if the frequency is applied to the abscissa and the strength of the filtering by the operators $\Lambda$ and $\Lambda^*$ to the ordinate, the total of both filter strengths at each frequency always produces the value 1. This applies to all frequencies, i.e. both the operators cover the entire frequency range and are standardized at 1. This complementary nature of both the filters is important in not shifting the CT values of the calculated images $f_k$ to higher or lower values; otherwise the water level of the CT images would be incorrect.

The application of $\Lambda$ and $\Lambda^*$ corresponds to frequency band decomposition. It provides selective access to which frequencies are intended to contribute in the convergence image PIC from the images PIC A and PIC B. The relative weighting of the frequency components is controlled by the parameters $\alpha_1$ and $\alpha_2$.

The correction term contains the differences between the current iteration image $f_k$ and the output images PIC A and PIC B. As the correction term is added to the current iteration image $f_k$, this corresponds to an approximation of the iteration image to both the output images PIC A and PIC B. However, this approximation only takes place in certain frequency ranges: as aforementioned, low-pass filtering is performed by the operator $\Lambda$. This corresponds to the properties of PIC A, according to which this image has a poor signal-to-noise ratio. As the noise is located in the high frequencies, their contribution to the iteration image $f_k$ is attenuated. The information concerning contrasts is found above all in the low-frequency range, these therefore being retained. On the other hand, $\Lambda^*$ corresponds to a high pass. This corresponds to the properties of PIC B, according to which this image has poor properties such as a shortage of spatial or time resolution or certain artifacts. These shortages are preferably found in the low image frequencies, so that their contribution to the iteration image should be reduced.

Iteration can be terminated after a certain number of iteration cycles or after reaching a termination or convergence criterion. The image $f_k$ resulting from the last iteration can then be displayed as the final image PIC.

The advantage of the iterative image reconstruction described is that in the final image PIC the positive parts of the image characteristic of both images PIC A and PIC B are combined. This may also be expressed in another way: on account of its advantageous properties, the image PIC A is the image which is of interest as the final image; by using the iterative algorithm the favorable signal-to-noise ratio of the image PIC B is transferred to the image PIC A. How well this transfer works depends in particular on the configuration of the filters Λ and Λ*, it being advantageous to adjust these filters to the image properties. Accordingly, the frequency range in which the positive properties of the image PIC A or the shortages of the image PIC B are located can be analyzed.

The use of the iteration in accordance with formula (I) aims to improve the signal-to-noise ratio of the image PIC A. However, its position sharpness should be retained in the process. In order to achieve this, the operator A can be adjusted to the sharpness of the image PIC A. To this end the frequency band decomposition characterized by the operator A is designed in such a way that the modulation transfer function (MTF) of the convolution kernel used for the reconstruction of the image PIC A is emulated. This modulation transfer function is determined by:

$$MTF = \frac{k(v)}{|v|} \quad \text{Formula (3)}$$

Here $k(v)$ is the frequency response of the CT convolution kernel used for the reconstruction of the image PIC A, i.e. the Fourrier transform of the position representation of the CT convolution kernel, and $v$ the frequency. For the operator Λ e.g. the following can then be selected:
Λ(v)=MTF(v), and on account of the aforementioned complementary property the following then applies:
Λ*(v)=1−MTF(v)

Other filter functions Λ, the threshold frequency of which corresponds to that of the modulation transfer function, are also possible. The rectangle function is particularly advantageous as in this case all frequencies are optimally transferred beneath the threshold frequency, in other words the frequency at which the modulation transfer function has the value 0.

The threshold frequency of the convolution kernel and therefore the modulation transfer function MTF(v) decides how sharp the resulting image PIC A is. The operator Λ is selected in such a way that it is just as good as the modulation transfer function MTF(v) with regard to sharpness. If the operator A were to decline at lower frequencies compared to MTF(v) this would mean a loss of position sharpness of the image PIC A through use of the iterative algorithm in accordance with formula (1). On the other hand, if the operator Λ were only to decline at higher frequencies compared to MTF (v), this would mean that a poorer signal-to-noise ratio would be expected for the final image, for on account of the configuration of the operator Λ* less of the good signal-to-noise ratio of the image PIC B would be transferred to the final image. By adjusting the operator A to the modulation transfer function MTF(v) the best possible position sharpness of the final image of the iterative algorithm is therefore guaranteed.

How the regularization operator ΛR can be arranged is described below. The object of the regularization contribution $\gamma \cdot \Lambda R(f_k)$ is to reduce the noise in the image so that convergence can be achieved during iteration. It can be shown that the architecture of the regularization operator alone is decisive for the noise characteristic of the final image.

The operator ΛR is therefore equivalent to a high pass so that on account of the minus sign before $\gamma \cdot \Lambda R(f_k)$ the effect corresponds to that of a low pass.

ΛR is a non-linear image filter. For if the entire image were only smoothed over homogeneously, although this would reduce the noise, the sharpness of the image would also be impaired as e.g. edges would also be softened. On the other hand, a non-linear image filter makes it possible both to reduce the noise and to retain the resolution. This happens when depending on the local contrast values smoothing takes place inside the image.

In the subsequently published German patent application by the applicant with the reference number 102010043975.4, the entire contents of which are hereby incorporated herein by reference in the present application, it is demonstrated how edge-preserving smoothing can take place in which fraying of the edges is also largely avoided. For after smoothing has been completed it very noticeable if the edges are not completely smooth; they then look grainy or frayed. This is achieved by reducing the smoothing effect orthogonally to an edge but keeping it to a maximum along the edge.

Regularization can be formulated as follows:

$$\nabla R(f)_i = \sum_j d_{ij} \Delta_{j,i} H\left( \frac{|\Delta_{j,i}|}{\sigma_i \cdot (1 + s(i) \cdot \kappa_{ij})} \right) \quad \text{Formula (3)}$$

Here $(f)_i$ is the i-th element of the image f, referred to as a pixel below for reasons of simplification. Summing takes place via the other pixels j; preferably summing only takes place via the immediate neighbors of the pixel i. Two-dimensionally these are 8 neighbors, three-dimensionally 26, and four-dimensionally 81. $d_{ij}$ is a high pass, defined e.g. by the inverse distance between the pixels i and j. This means that a pixel contributes less the greater its distance from the pixel i. The so-called domain filter $d_{ij}$ guarantees the high-pass characteristic of the regularization contribution. $\Lambda_{j,i}$ is the grayscale value distance between the pixels i and j, i.e. $\Lambda_{j,i} = f_i - f_j$. This corresponds to the contrast.

$\sigma_i$ is the isotropic local noise at the location of the pixel i. This variable can e.g. be determined by determining the variance along lines in accordance with the connections to the immediate neighbors of the pixel i, and ascertaining the minimum of these variances. If $\sigma_i$ is equated to this minimum then there is a high probability that any existing physical structure will not be regarded as noise inadvertently.

The variable s(i), the significance at the location of the pixel i, is a measure for the presence of an object edge at the location of the pixel i. If such an object edge is not present, it has the value 0, in the case of one edge it has the value 1. Between these two extremes it increases monotonously.

The variable $\kappa_{ij}$, the deformation strength of the image, is a function of the angle between the direction vectors of the connection between the pixels i and j on the one hand and the local prototype gradient in the pixel i. This variable ascertains the curve of the edge by calculating gradients along a detected edge.

The characteristic curve H is referred to as an influence function; in general it is the case that the influence function displays the value 1 depending on its argument at 0 and then falls off constantly in a non-linear manner. In the case of a major argument, it is 0 or even negative.

The argument of the influence function is therefore a modified local contrast-to-noise ratio. The greater this is, the smaller the value of the influence function, and accordingly the less filtering or smoothing there is at this point in the image. In the case of minor contrasts, on the other hand, major filtering takes place.

Advantageous examples of this configuration of the influence function, and of s(i) and $\kappa_{ij}$ can be found in the aforementioned subsequently published application.

Deviating from the equation (2) other formulations of the regularization operator can also be used. An example is a Laplace filter. Preferably the filter used for regularization should bring about non-linear and therefore edge-retaining smoothing of the image. An example of this is described in the publication DE 10 2009 039 987 A1.

Example embodiments of the iterative image reconstruction described are explained below.

EXAMPLE 1

Dual Energy Measurements

The aim of dual energy measurements is usually to be able to undertake material segmentation. For example, iodine and bone can be distinguished in this way. Low noise simplifies the calculation of material decomposition. For this reason the CT images are usually reconstructed with a soft convolution kernel, resulting in low-noise images. However, these smoothed images have extremely limited spatial resolution. This results in the erroneous assignment of pixels to materials in some areas of the image. It would therefore be desirable to improve the contrast-to-noise of the images in order to be able to undertake error-free material segmentation.

After the dual energy CT measurement and a first image reconstruction, there are two CT images present, a first one for the first X-ray tube voltage (e.g. 80 kV), and a second one for the second X-ray tube voltage (e.g. 140 kV). The image of the first X-ray tube voltage is now used for the image PIC A; this image has the advantage of good spectral resolution. For the image PIC B on the other hand, a weighted average of the two images is calculated. As the two images are statistically independent of each other, the resulting image has a good signal-to-noise ratio; the spectral resolution is lost as a result of the combination. The weighting may be dependent on the type of tissue concerned.

Now iterative image reconstruction takes place in accordance with the formula (1). The result is an image for the first X-ray tube voltage, which has high spectral resolution and a good signal-to-noise ratio.

This same approach is now repeated with regard to the image of the second X-ray tube voltage. As a result there are sharp images with a good signal-to-noise ratio for both X-ray energies.

EXAMPLE 2

High-Resolution CT Measurement

A CT measurement of the detector channels is taken with a standard aperture, as well as a measurement and a high-resolution measurement with a reduced aperture. Such a reduction of the detector aperture makes it possible to obtain spatial high-resolution images. CT images are reconstructed from both measurements. With the standard measurement, in contrast to the high-resolution measurement there is limited spatial resolution but a better signal-to-noise ratio as quanta are lost as a result of the reduced aperture.

High-resolution measurement is used for the image PIC A and standard measurement for the image PIC B. Iterative image reconstruction in accordance with the formula (1) results in a high-resolution image with reduced noise.

EXAMPLE 3

Perfusion Measurements, in Particular Cardiac Perfusion Measurements

After administration of the contrast agent, CT measurement data is recorded at consecutive time points, and accordingly a series of chronologically consecutive images is reconstructed, in other words, images for several so-called time frames. In order to minimize the dose, measurement takes place at relatively low X-ray intensity. Therefore the images are noisy.

One of these individual images is used as image PIC A; it has temporal high-resolution, but on account of the aforementioned dose reduction it has a poor signal-to-noise ratio. The sum—if applicable weighted—of several or all of the images in the series comprises image PIC B; this composite image has a high signal-to-noise ratio on account of the statistical independence of the individual images. The iterative image reconstruction in accordance with formula (1) produces a temporal high-resolution image with a good signal-to-noise ratio.

EXAMPLE 4

Improved Dose Use in Cardiac CT

Spatiotemporal measurement data is available. In other words, the moving heart was measured during a cardiac cycle, redundant data is therefore measured for retrospective phase selection so that the same image position can be reconstructed in different cardiac phases. Usually the optimum cardiac phase for timely display of the coronary vessels is determined. As phase selection, i.e. the decision about which phase is assessed as the final image in the end, only takes place afterwards, a high tube current is used in an extended phase range. Accordingly, the examination object is exposed to a high dose during measurement. It is therefore desirable to make full use of the applied dose during image reconstruction.

The timely image of the optimum cardiac phase is used as image PIC A. In order to obtain high temporal resolution, the smallest possible data area is used for this reconstruction. This corresponds to a projection angle area of 180° plus the fan angle of the X-ray beam. On the other hand, an extended data area is used to reconstruct the image PIC B. This also contains the measurement data which was used for the reconstruction of the image PIC A. As a result of this, the time resolution of the image PIC B is significantly worse but there is an enhanced signal-to-noise ratio. As a result of this, the entire applied dose was "transferred" to the image PIC B.

By using the formula (1), a temporal high-resolution image with reduced noise is obtained. Without loss of time resolution the enhanced quanta statistics of the image PIC B are therefore transferred to the temporal high-resolution image PIC A.

Figure 4:
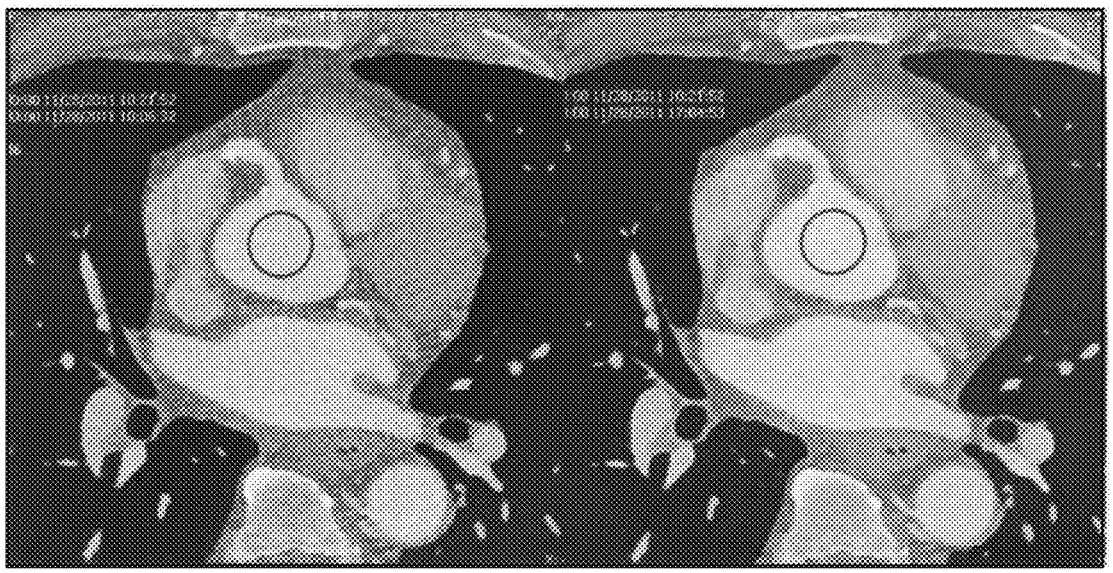
FIG. 4: two cardiac CT images.

To illustrate example 4, FIG. 4 shows two CT images of the human heart. For the image on the left $\alpha_1$ and $\alpha_2$ were equated to 0, and $\gamma=0.9$ and in addition, PIC A=PIC B was used; i.e. only the non-linear image filter in accordance with the regularization term was applied to the high-resolution image PIC A. In this way, noise reduction of 40% is obtained in the region demarcated by a circle compared with the unfiltered image PIC A. For the image on the right $\alpha_1=0.95$ $\alpha_2=0.15$, γ=0.5 was used; PIC B was reconstructed from a data area twice as large as PIC A. In this way noise reduction of 66% is obtained in the region demarcated by a circle compared with the unfiltered image PIC A.

EXAMPLE 5

Phase Contrast CT

CT images enable absorption differences to be shown in objects; however, areas of similar chemical composition which also inherently display similar absorption characteristics are sometimes only shown in insufficient detail. In order to avoid this the use of phase contrasts is proposed. In the phase contrast CT a "shift" is measured as the phase relationship of X-rays changes slightly when they penetrate an examination object. The effect of the phase shift when an X-ray passes through an examination object is considerably stronger than the absorption effect of the matter penetrated by the radiation: the difference in the phase shift through different densities of tissue is approximately one hundred times greater than the different absorption in soft and hard material.

The skilled construction of several grids must be used for this purpose. Before the X-ray source at least one source grid is used in the ray path to generate quasi-coherent radiation, and after the examination object on the detector side there may be several grids, such as e.g. interference grids, phase and analysis grids. The devices and evaluation methods of the phase contrast CT are described, for example, in the documents DE 10 2006 037 255 A1, DE 10 2006 017 291 A1, DE 10 2006 015 358 A1, and DE 10 2006 015 356 A1, the entire contents of each of which are hereby incorporated herein by reference.

A traditional CT image is used as an image PIC A, and a phase contrast image as image PIC B. Both the images PIC A and PIC B may originate from the same measurement. For in phase contrast CT both a phase contrast CT image and a "classic" absorption CT image can be calculated from the measured signal. Alternatively, it is possible to obtain the measurement data for the image PIC B by means of a phase contrast CT device, and the measurement data for the image PIC A by means of a traditional CT device.

The image PIC B exhibits noise in the low-frequency range, which is extremely disruptive for diagnosis as the noise spots of actual object lesions can only be distinguished with difficulty or not at all. In traditional absorption CT, in other words in the image PIC A, this low-frequency noise component does not exist. At the other frequencies, however, the image PIC B is characterized by an enhanced signal-to-noise ratio compared with the image PIC A. By using the formula (1) an image with high spatial resolution is obtained, corresponding to the properties of the phase contrast image, but which does not exhibit any increased noise in the low-frequency range.

EXAMPLE 6

Multiphase CT Examinations

This example is described below with reference to a liver examination; however, the approach is also applicable to other examination objects. In CT examinations of the liver 2-phase or 3-phase protocols are often used. This means that a first quantity of measurement data is acquired initially, producing the so-called native image. Subsequently a contrast agent is administered to the patient, whereupon a second quantity of measurement data is acquired, and if necessary a third and further quantities of measurement data are acquired. The second image is the so-called arterial image, the third the so-called venous image of the liver. Phase-delayed contrast agent permeation results in time-dependent contrasting of lesions. In order to avoid spatial blurring, registration of the individual images from the various phases is important.

In order not to expose the patient to an excessive dose of radiation, when taking the measurements efforts are made to use low-intensity irradiation. This results in a poor signal-to-noise ratio of the individual images. At the same time, however, endeavors are made to achieve good detectability of the lesions.

A linear combination of the image data from native, arterial, venous and if necessary, further late phases are used as image PIC B:

$$PICB = w_1 \cdot f_{native} + \sum_{k=2}^{N} w_k \cdot f_k, \text{ where } \sum_{k=1}^{N} w_k = 1$$

Here $f_{nativ}$ represents the native image, and $f_k$ where k≥2 the images of the following phases, the last image bearing the index N. In the case of the coefficients $w_k$, in the simplest case, figures may be involved. However, it is advantageous to use not scalars but image matrices as coefficients. As a result of this, each pixel of the images $f_k$ is multiplied by the associated value of the matrix $w_k$; there is therefore a local variable weighting of the images in the linear combination.

The image PIC B has an enhanced signal-to-noise ratio compared with the individual images $f_{native}$ and $f_k$ on account of the statistical independence of the images. As a result of the fact that for the calculation of PIC B no pure average imaging takes place via the images $f_{native}$ and $f_k$ but a weighted summation, it is possible that images with a good signal-to-noise ratio contribute more to PIC B than images with a poor signal-to-noise ratio. The same also applies to local weighting when using matrices $w_k$.

An individual image, in other words $f_{native}$ and $f_k$, is used as image PIC A in each case. The iterative algorithm is therefore applied to each of the individual images. By using the algorithm based on the formula (1), an enhanced signal-to-noise ratio can be obtained for the individual images while spatial resolution remains the same. As a result of this, the recognition of lesions is increased.

With the multiphase liver CT, in particular the Arterial Enhancement Fraction (AEF) is a variable relevant to evaluation. On account of the equation $$AEF = \frac{f_{arterial} - f_{native}}{f_{venous} - f_{native}}$$

the AEF is strongly influenced by the image noise so that the improvement of the signal-to-noise ratio has a significant effect on the AEF.

EXAMPLE 7

Subtraction Angiography CT

In subtraction angiography CT, a CT image is reconstructed from a first measurement, the so-called native image $f_{native}$. Subsequently, after a contrast agent has been administered, another measurement is performed, and a further CT image $f_{iodine}$ is reconstructed from this. Both the images are subtracted in order to make the vessels visible. For as a result of difference imaging, bone structures and/or vascular calcification disappear. However, this difference imaging impairs the signal-to-noise ratio so that the display of the vessels is noisy.

In order to avoid spatial blurring, registration of both the images is important. It is possible to subtract not the entire images but only the segments matching the image data from each other.

A linear combination of the two images $f_{native}$ and $f_{iodine}$ is used as image PIC B:

$$PICB = w_1 \cdot f_{native} + w_2 \cdot f_{iodine}, \text{ where } w_1 + w_2 = 1$$

As far as the weighting factors $w_1$ and $w_2$ are concerned, as already explained in Example 6 with regard to $w_k$, matrices which bring about location-dependent weighting may be involved.

For the image PIC A the difference between the images $f_{native}$ and $f_{iodine}$ is used. Alternatively, separate optimization of $f_{native}$ and $f_{iodine}$ may also be performed by using $f_{native}$ once and $f_{iodine}$ once as image PIC A. Difference imaging then takes place after the use of the iterative algorithm in accordance with the equation (1).

The aforementioned example embodiments relate to the medical application of the invention. However, embodiments of the invention may also be used outside the field of medicine, for example for baggage inspection or materials testing.

The invention was described above using an exemplary embodiment. It goes without saying that numerous amendments and modifications are possible without departing from the context of the invention.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims.

Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstruction of image data of an examination object from measurement data, wherein the measurement data for a relative rotational movement between a radiation source of a computed tomography system and the examination object are recorded, the method comprising:
    reconstructing first image data with a first image characteristic and second image data with a second image characteristic from the measurement data, a signal-to-noise ratio of the second image characteristic being relatively enhanced as compared to the first image characteristic; and
    calculating enhanced image data using the first and the second image data and using an iterative algorithm, wherein in the iterative algorithm,
    a low pass filter is applied to a difference between the first image data and image data of an iteration cycle, and
    a high pass filter is applied to a difference between the second image data and the image data of the iteration cycle.

2. The method of claim 1, wherein the enhanced image data includes an enhanced signal-to-noise ratio compared with the first image data.

3. The method of claim 1, wherein, in the iterative algorithm, a non-linear operator is applied to the image data of the iteration cycle, which performs edge-retaining smoothing.

4. The method of claim 3, wherein the non-linear operator comprises:
    a filtering dependent on a contrast-to-noise.

5. The method of claim 3, wherein, in the iterative algorithm, the image data of the iteration cycle and results of, applying the low pass filter to the difference between the first image data and the image data of the iteration cycle, applying the high pass filter to the difference between the second image data and the image data of the iteration cycle, and applying the non-linear operator are added.

6. The method of claim 1, wherein the first image data includes at least one of,
    relatively better spatial resolution than the second image data,
    relatively better temporal resolution than the second image data,
    relatively better spectral resolution than the second image data, and
    relatively fewer image artifacts than the second image data.

7. The method of claim 1, wherein the second image data is used as image data of the zero-th iteration.

8. The method of claim 1, wherein the measurement data is recorded using a dual-energy measurement,
    image data for a first X-ray energy and image data for a second X-ray energy are reconstructed,
    the first image data corresponds to the image data of the first X-ray energy, the second image data corresponds to a combination of the image data of the first X-ray energy and the image data of the second X-ray energy, and the enhanced image data of the first X-ray energy is calculated using the iterative algorithm.

9. The method of claim 8, wherein the first image data subsequently corresponds to the image data of the second X-ray energy, the second image data corresponds to the combination of the image data of the first and the image data of the second X-ray energy, the enhanced image data of the second X-ray energy is calculated using the iterative algorithm, and the method further comprises:
performing a segmentation of the enhanced image data based on the enhanced image data of the first X-ray energy and the enhanced image data of the second X-ray energy.

10. The method of claim 1, wherein a first quantity of measurement data is acquired and a second quantity of measurement data is acquired, the second quantity of measurement data acquired is a high-resolution measurement with a reduced detector aperture, the first image data is reconstructed from the measurement data of the second measurement data acquisition and the second image data is reconstructed from the measurement data of the first measurement data acquisition.

11. The method of claim 1, wherein a perfusion measurement takes place, image data corresponding to a series of consecutive time points is reconstructed, the first image data corresponds to one element of the series, and the second image data corresponds to a combination of several elements of the series.

12. The method of claim 11, wherein the method is performed with respect to a plurality of individual elements in the series.

13. The method of claim 1, wherein the measurement data is acquired during a movement of the examination object, the first image data is reconstructed from a first segment of the measurement data, and the second image data is reconstructed from an enlarged segment of the measurement data compared to the first image data.

14. The method of claim 13, wherein the first segment corresponds to a minimum measurement data area required for the reconstruction of the image data.

15. The method of claim 1, wherein the first image data corresponds to an absorption CT image and the second image data corresponds to a phase contrast CT image.

16. The method of claim 1, wherein a first quantity of measurement data is acquired before a contrast agent is administered, and at least one additional quantity of measurement data is acquired after the contrast agent is administered, from the measurement data of the first measurement data acquisition native image data, and from the measurement data of at least one additional measurement data acquisition, one or more additional items of image data are reconstructed, the first image data corresponds to the native image data or to one of the one or more additional items of image data, and the second image data corresponds to a combination of the first image data with the one or more additional items of image data.

17. The method of claim 16, wherein the combination is a weighted total with a location-dependent weighting.

18. The method of claim 1, wherein a first quantity of measurement data is acquired before a contrast agent is administered, and an additional quantity of measurement data is acquired after the contrast agent is administered, from the measurement data of the first measurement data acquisition native image data, and from the measurement data of the additional measurement data acquisition additional image data is reconstructed, the first image data corresponds to a difference between the native image data and the additional image data, and the second image data corresponds to a combination of the first image data with the additional image data.

19. The method of claim 18, wherein the combination is a weighted total with a location-dependent weighting.

20. The method of claim 1, wherein a first quantity of measurement data is acquired before a contrast agent is administered, and a further quantity of measurement data is acquired after the contrast agent is administered, native image data is reconstructed from the measurement data of the first quantity of measurement data acquired, and additional image data from the measurement data of the additional quantity of measurement data acquired, the first image data corresponds to the native image data, the second image data corresponds to a combination of the first image data with the additional image data, and first enhanced image data is calculated using the iterative algorithm, the first image data corresponds to the additional image data, the second image data corresponds to a combination of the first image data with the additional image data, and second enhanced image data is calculated using the iterative algorithm, and a difference between the first image data and the second enhanced image data is calculated.

21. The method of claim 20, wherein the combination is a weighted total with a location-dependent weighting.

22. The method of claim 1, wherein the low pass filter is adjusted to a modulation transfer function of the first image data.

23. The method of claim 1, wherein the high pass filter is designed as a complementary filter to the low pass filter.

24. A device configured to reconstruct image data of an examination object from measurement data, wherein the measurement data for a relative rotational movement between a radiation source of a computed tomography system and the examination object are recorded, the device comprising:

a processor configured to,
reconstruct first image data with a first image characteristic and second image data with a second image characteristic from the measurement data, a signal-to-noise ratio of the second image characteristic being relatively enhanced as compared to the first image characteristic; and calculate enhanced image data using the first and the second image data and using an iterative algorithm, wherein in the iterative algorithm, a low pass filter is applied to a difference between the first image data and image data of an iteration cycle, and a high pass filter is applied to a difference between the second image data and the image data of the iteration cycle.

25. A CT system comprising: the device of claim 24.

26. A non-transitory computer readable medium including computer readable instructions, which when executed by a processor, causes the processor to reconstruct image data of an examination object from measurement data, wherein the measurement data for a relative rotational movement between a radiation source of a computed tomography system and the examination object are recorded, the processor reconstructing the image data by:
- reconstructing first image data with a first image characteristic and second image data with a second image characteristic from the measurement data, a signal-to-noise ratio of the second image characteristic being relatively enhanced as compared to the first image characteristic; and
- calculating enhanced image data using the first and the second image data and using an iterative algorithm, wherein in the iterative algorithm,
- a low pass filter is applied to a difference between the first image data and image data of an iteration cycle, and
- a high pass filter is applied to a difference between the second image data and the image data of the iteration cycle.

* * * * *